(12) United States Patent
Morikawa et al.

(10) Patent No.: US 7,716,697 B2
(45) Date of Patent: May 11, 2010

(54) INFORMATION PROCESSING SYSTEM, INFORMATION PROCESSING APPARATUS, AND METHOD

(75) Inventors: Koji Morikawa, Kyoto (JP); Shinobu Adachi, Osaka (JP)

(73) Assignee: Panasonic Corporation, Kadoma (JP)

( * ) Notice: Subject to any disclaimer, the term of this patent is extended or adjusted under 35 U.S.C. 154(b) by 446 days.

(21) Appl. No.: 11/577,883

(22) PCT Filed: Sep. 12, 2006

(86) PCT No.: PCT/JP2006/318016

§ 371 (c)(1),
(2), (4) Date: Apr. 25, 2007

(87) PCT Pub. No.: WO2007/066440

PCT Pub. Date: Jun. 14, 2007

(65) Prior Publication Data

US 2009/0147148 A1 Jun. 11, 2009

(30) Foreign Application Priority Data

Dec. 8, 2005 (JP) .............................. 2005-354309

(51) Int. Cl.
*H04H 60/33* (2008.01)
*A61B 5/04* (2006.01)

(52) U.S. Cl. ........................... 725/10; 725/12; 600/544; 600/545

(58) Field of Classification Search ................... 725/10; 600/544–545
See application file for complete search history.

(56) References Cited

U.S. PATENT DOCUMENTS 4,932,416 A * 6/1990 Rosenfeld ................... 600/544
5,243,517 A * 9/1993 Schmidt et al. ............. 600/544
5,449,978 A 9/1995 Matsuda et al.

(Continued)

FOREIGN PATENT DOCUMENTS

JP 01-230343 9/1989

(Continued)

OTHER PUBLICATIONS

Schiffer et al., Neuropsychiatry, 2nd Edition, p. 71.*

(Continued)

*Primary Examiner*—Brian T Pendleton
*Assistant Examiner*—Fernando Alcon
(74) *Attorney, Agent, or Firm*—Renner, Otto, Boisselle & Sklar, LLP

(57) ABSTRACT

There is provided a technique which, in the case where the operation has not occurred in a manner as expected by the user, determines from which standpoint the operation was not as expected, and makes a response that is closer to the expectation.

An information processing system according to the present invention includes: a reaction section for executing a first process based on a request from a user; an output section for outputting a result of a process; a signal detection section for measuring a signal concerning an event-related potential of electroencephalograms of the user; an analysis section for identifying a positive peak in the event-related potential and determining whether an elapsed time since the result is output and until the peak appears is closer to a first reference time or a second reference time; and a reaction modifying section for determining a second process in accordance with the determination result. This determination result indicates a degree of disappointment of the user, and the second process is to be determined in accordance with the degree. By the reaction section executing the second process, an operation is realized which conforms to the user's expectation even if the operation has not occurred in a manner as expected by the user.

8 Claims, 12 Drawing Sheets

U.S. PATENT DOCUMENTS

| | | | |
|---|---|---|---|
| 5,635,989 A * | 6/1997 | Rothmuller | 725/46 |
| 6,254,536 B1 * | 7/2001 | DeVito | 600/544 |
| 7,536,270 B2 * | 5/2009 | Morikawa et al. | 702/127 |
| 2002/0178440 A1 * | 11/2002 | Agnihotri et al. | 725/10 |
| 2003/0013981 A1 * | 1/2003 | Gevins et al. | 600/544 |
| 2004/0073129 A1 * | 4/2004 | Caldwell et al. | 600/544 |
| 2004/0097824 A1 * | 5/2004 | Kageyama | 600/544 |
| 2006/0101079 A1 | 5/2006 | Morikawa et al. | |

FOREIGN PATENT DOCUMENTS

| | | |
|---|---|---|
| JP | 05-211097 | 8/1993 |
| JP | 11-288341 | 10/1999 |
| JP | 2003-058298 | 2/2003 |
| JP | 2004-86768 | 3/2004 |
| WO | 2005/001677 | 1/2005 |

OTHER PUBLICATIONS

International Search Report for corresponding Application No. PCT/JP2006/318016 mailed Dec. 12, 2006.

Form PCT/ISA/237 and a concise explanation.

* cited by examiner

FIG.1
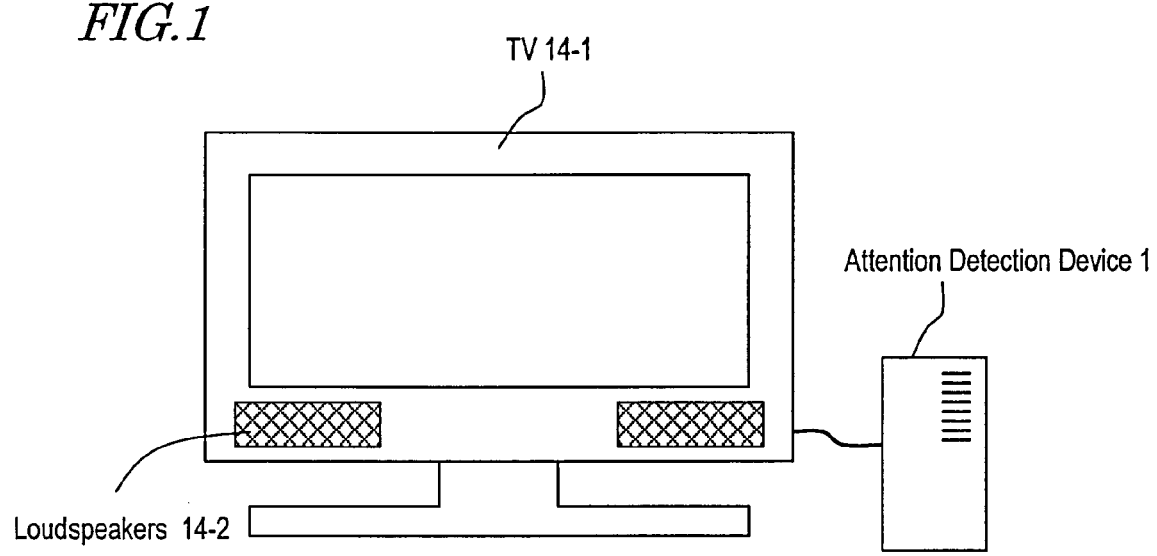
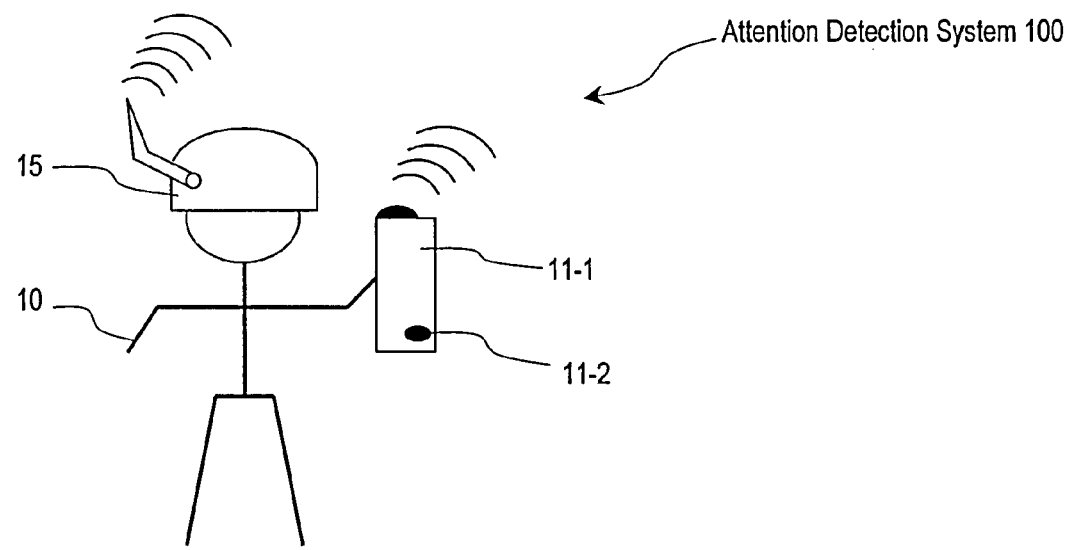

FIG.5

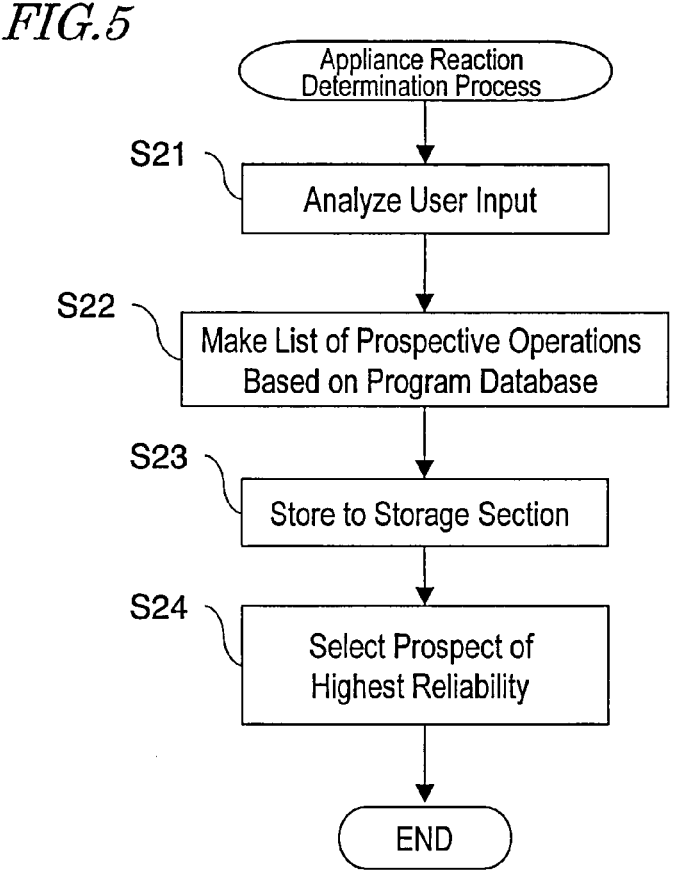

FIG.6

| Prospective Operation \ Request Example | "Turn on the TV" | "I Want to Watch Baseball" | "Get Me That" |
|---|---|---|---|
| | 41 | 42 | 43 |
| 1 | Adopted: News X | Adopted: Professional Baseball | Adopted: Newspaper |
| 2 | Same: News Y | Same: Major League | Different: Glasses |
| 3 | Different: Weather Forecast C | Different: Video of Sandlot Baseball Team | Same: Mail |
| 4 | Different: Animation A | - | Different: Tea |

Adopted: Prospective Operation Having Highest Reliability and being Adopted as Output Operation
Same: Belongs to Same Category as Adopted Prospect
Different: Belongs to Different Category from Adopted Prospect

FIG.10

Q1. Switch to 2ch

A: 2ch    B: 4ch
C: 10ch    D: 8ch (a) Question Type 1 (Designate Channel No.)

Q2. Switch to Animation

A: Baseball    B: Weather Forecast
C: Animation    D: News (b) Question Type 2 (Designate Genre)

Q3. Switch to News X

A: News Z    B: News Y
C: Animation A    D: News X (c) Question Type 3 (Designate Program Title)

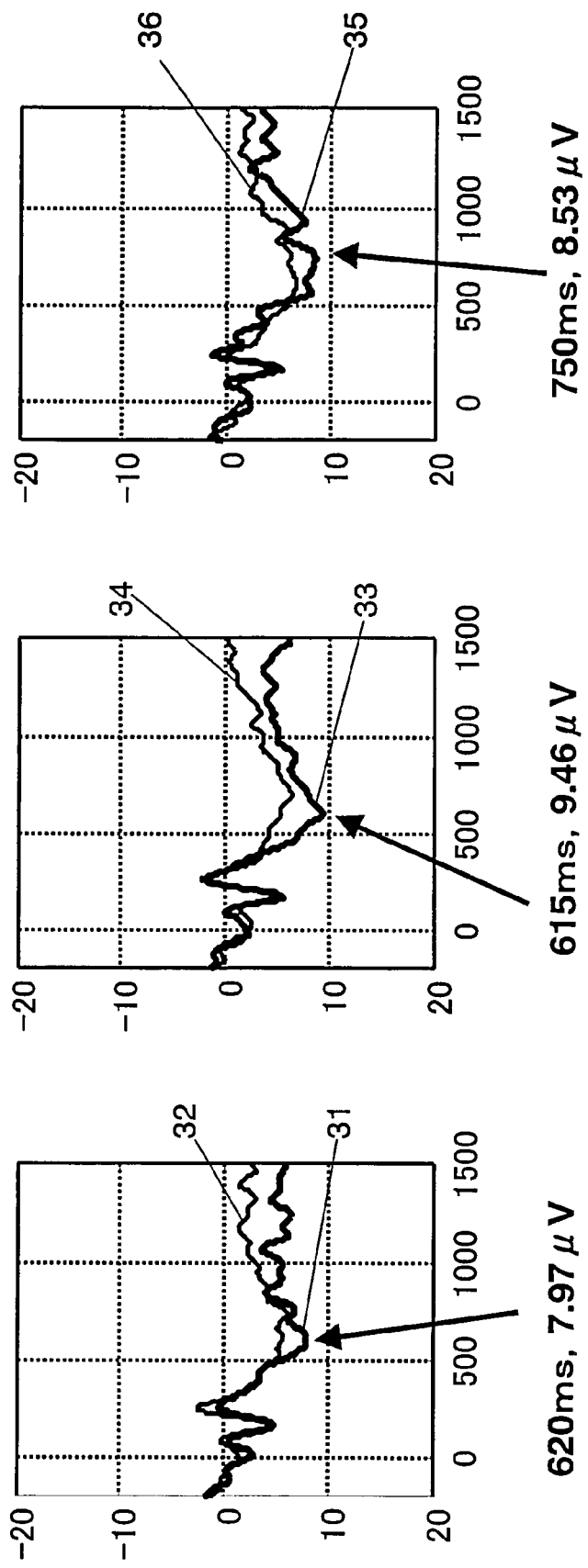

INFORMATION PROCESSING SYSTEM, INFORMATION PROCESSING APPARATUS, AND METHOD

TECHNICAL FIELD

The present invention relates to a technique of providing information or services for a user. More specifically, the present invention relates to an appliance or method which utilizes a biological signal, e.g., electroencephalograms of a user, to select and provide appropriate information or services, and a computer program to be executed on such an appliance.

BACKGROUND ART

In recent years, the amount of information (content) which is handled by an information appliance or a video/audio appliance has become enormous. Therefore, unless the user gives an instruction to the appliance by precisely specifying a content, the appliance cannot provide appropriate contents.

For example, an appliance has been proposed which, when a user wishes to watch a video of baseball, receives and displays a desired baseball program if the user gives an instruction that he or she "wants to watch baseball". This appliance operates by assuming that the video of baseball that the user wishes to watch is a baseball program which is being broadcast at that point in time. In the days when this proposal was made, the appliance was sufficiently able to meet the user's expectation by such an operation. Currently, however, the video related to baseball are diversified. For example, Japanese professional baseball programs, high school baseball programs, US major league programs, and even video of last week's game of a sandlot baseball team to which the user belongs may be a target of viewing. Therefore, unless the user gives an instruction that precisely specifies which baseball he or she wants to watch, the appliance cannot provide a video of baseball as desired by the user.

In order to give an instruction of a specified content to an appliance, the user is required to perform very complicated tasks. Therefore, how the tasks can be reduced will become an important index that determines the performance of the appliance.

For example, if a request containing ambiguity is received from the user, it is preferable that the appliance is able to provide the user with a content which is considered appropriate. Moreover, if the selection that has been made by the appliance does not suit the user's intention, it is preferable that the appliance recognizes the situation and performs a process of providing a more appropriate content. For example, an increased convenience will be obtained if the appliance is able to request to the user for further information concerning the content, or if the appliance is able to select and provide another content based on the history of user manipulations or the like.

Patent Document 1 discloses a service providing apparatus which infers the user's intention based on the electroencephalograms of the user, and controls its own operation. After responding to a request of the user, this apparatus detects a biological signal of the user. Then, from this signal, it infers whether the response content has resulted in a disappointment or not, and upon determining a disappointment, modifies the response content.

[Patent Document 1] International Laid-Open No. WO2005/001677

DISCLOSURE OF INVENTION

Problems to be Solved by the Invention

Although the conventional appliance modifies the response content based on a biological signal from the user, it is unknown whether or not the modified content will match the user's expectation. The reason is that the appliance does not take into consideration how the response content should be modified. The appliance merely makes a binary determination as to whether the response content has proven to be a disappointment to the user, and does not analyze from which standpoint the user has regarded its content to be a disappointment. Therefore, it is possible that the modified content may also prove to be a disappointment to the user.

An object of the present invention is to provide a technique which, even when a user has input a request which contains ambiguity, will operate in accordance with the user's expectation as much as possible. In particular, an object of the present invention is to provide a technique which, in the case where the operation has not occurred in a manner as expected by the user, determines from which standpoint the operation was not as expected, and makes a response that is closer to the expectation.

Means for Solving the Problems

An information processing system according to the present invention comprises: a reaction section for executing a first process based on a request from a user; an output section for outputting a result of a process; a signal detection section for measuring a signal concerning an event-related potential of electroencephalograms of the user; an analysis section for determining whether an elapsed time since the result is output and until a positive peak in the event-related potential appears is closer to a first reference time or a second reference time; and a reaction modifying section for determining a second process in accordance with the determination result. The reaction section executes a second process.

The analysis section may make the determination by defining the first reference time to be 600±50 milliseconds and the second reference time to be 750±50 milliseconds.

The information processing system may further comprise a storage section for retaining a plurality of parameters to be used for executing a process. The plurality of parameters are each categorizable into a plurality of categories. The reaction modifying section may be operable to: select a parameter belonging to a different category from that of the parameter used for the first process, when receiving a determination result indicating that the elapsed time is close to the first reference time of 600±50 milliseconds; select a parameter belonging to the same category as that of the parameter used for the first process, when receiving a determination result indicating that the elapsed time is close to the second reference time of 750±50 milliseconds; and determine a process using the selected parameter as the second process.

The storage section may retain history information indicating a frequency of use of each parameter; and the reaction section may select a parameter based on the history information, and execute the first process by using the selected parameter.

The reaction modifying section may determine the second process by selecting, among the parameters which are yet to be selected, a parameter having a highest frequency of use.

In response to execution of the second process, the storage section may update the history information of the parameter used for the second process.

Regarding a first content and a second content including at least one of video and audio, the reaction section may execute an outputting process of the first content as the first process, and execute an outputting process of the second content which is different from the first content as the second process.

An information processing apparatus according to the present invention is connected to an input device, an output device, and a signal detection device. The input device includes means for receiving a request from a user; the output device includes means for outputting a received signal; and the signal detection device includes means for measuring a signal concerning an event-related potential of electroencephalograms of the user. The information processing apparatus comprises: a reaction section for executing a first process based on the request of the user from the input device and outputting a signal; an analysis section for, based on the signal concerning the event-related potential, identifying a positive peak in the event-related potential, and determining whether an elapsed time since the result is output and until the peak appears is closer to a first reference time or a second reference time; and a reaction modifying section for determining a second process in accordance with the determination result. The reaction section outputs a signal by executing the second process.

An information processing method according to the present invention comprises the steps of: executing a first process based on a request from a user; outputting a result of a process; measuring a signal concerning an event-related potential of electroencephalograms of the user; identifying a positive peak in the event-related potential; determining whether an elapsed time since the result is output and until the peak appears is closer to a first reference time or a second reference time; determining a second process in accordance with the determination result; and executing a second process.

A computer program according to the present invention is executable on a computer. The computer program is recorded on a storage medium, and read by a computer. The computer program having been read causes the computer to execute the steps of: executing a first process based on a request from a user which is input from an input device; outputting a result of a process to an output device; receiving a signal concerning an event-related potential of electroencephalograms of the user which is detected by a detection device; identifying a positive peak in the event-related potential; determining whether an elapsed time since the result is output and until the peak appears is closer to a first reference time or a second reference time; executing a second process in accordance with the determination result.

EFFECTS OF THE INVENTION

According to the present invention, when a user feels a disappointment, the nature of a signal indicating the disappointment is determined. Based on the determination result, an operation of an appliance is modified. Since the operation of the appliance is modified so as to conform to the target which the user has been paying attention to, a result which conforms to the user's expectation can be provided for the user.

BRIEF DESCRIPTION OF DRAWINGS

FIG. 1 A diagram showing an exemplary construction of an attention detection system 100.

FIG. 5 A flowchart showing the procedure of processes by the appliance reaction section 12.

FIG. 6 A diagram showing a list 41 of prospective operations which is generated by the appliance reaction section 12.

FIG. 10 A diagram showing example questions used in the experiment.

FIG. 13 (a) to (c) are graphs showing analysis results of experimental data for question types 1 to 3, respectively.

Figure 2:
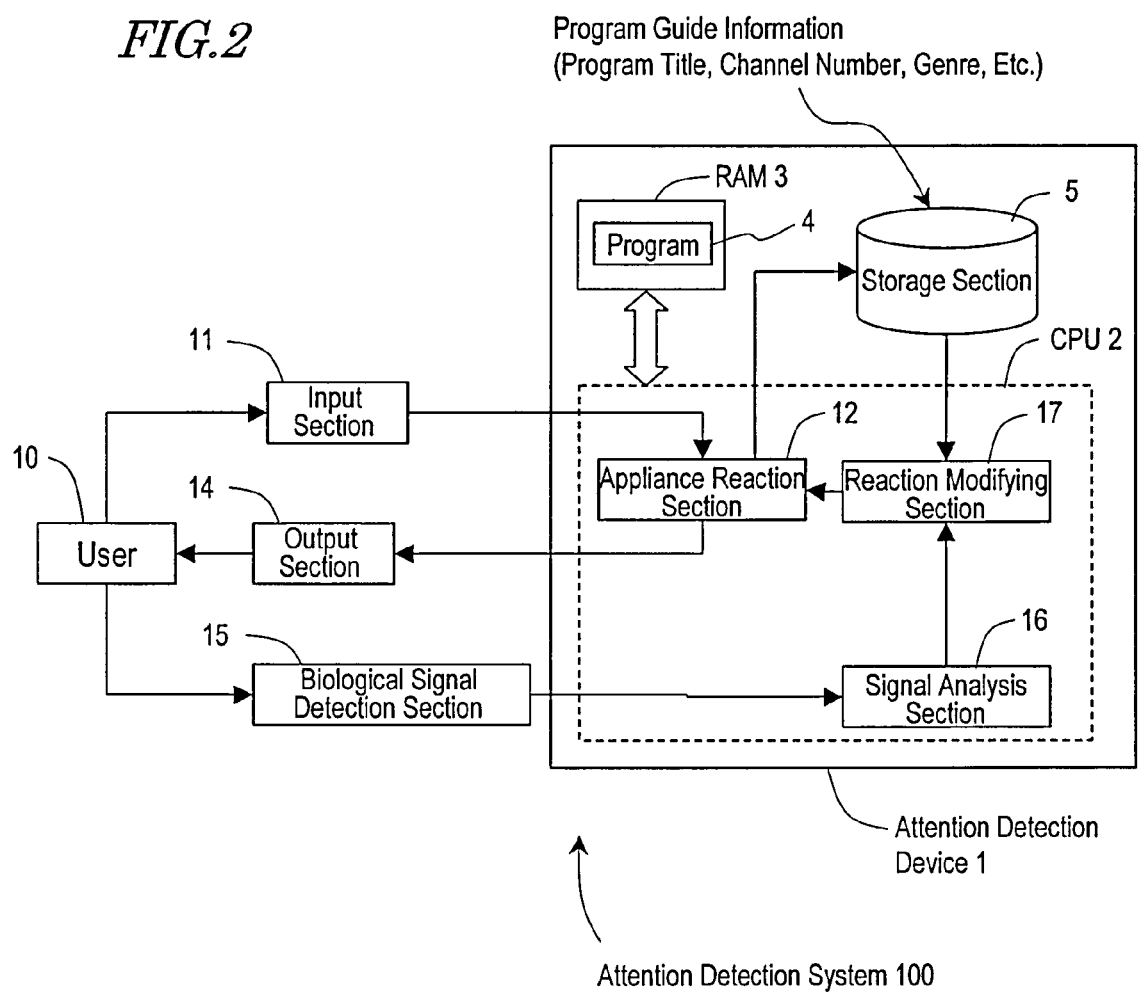
FIG. 2 A diagram showing the functional block construction of the attention detection system 100.

DESCRIPTION OF THE REFERENCE NUMERALS 1 attention detection device
2 CPU
3 RAM
4 computer program
5 storage section
10 user
11 input section
12 appliance reaction section
14 output section
15 biological signal detection section
16 signal analysis section
17 reaction modifying section
100 attention detection system

BEST MODE FOR CARRYING OUT THE INVENTION

Hereinafter, with reference to the attached drawings, an embodiment of an information processing system and information processing apparatus according to the present invention will be described.

In the present embodiment, a process which utilizes an event-related potential (ERP) of the user's electroencephalograms will be described. An "event-related potential" is a portion of the electroencephalograms, referring to a transient potential fluctuation in the brain which occurs in temporal relationship with an external or internal event.

The inventors have found that, when an appliance has not operated in a manner as expected by the user, a characteristic feature appears in an event-related potential of the user's electroencephalograms. More specifically, a predetermined peak appears in the waveform of an event-related potential of the user, at the time of 600±50 milliseconds or 750±50 milliseconds since a point in time at which an operation result is presented.

Since such a difference in time was observed even while the same user was watching the same content, the inventors conducted a further analysis to find that the difference in time occurs depending on the target to which the user is paying attention. For example, this means that the time at which the aforementioned peak appears will differ depending on whether the user has felt, regarding the same content that has been presented by the appliance, that the genre itself is wrong or that the genre is correct but the content is wrong, etc.

Therefore, by determining whether the time at which such a peak appears is closer to 600±50 milliseconds or 750±50 milliseconds since the point in time at which the operation result was presented, it is possible to detect from which standpoint the presented content has been regarded as a disappointment. Then, based on this determination, it can be determined how the operation of the appliance should be modified.

Hereinafter, an experiment which has been performed by the inventors will be described with reference to FIG. 9 to FIG. 13, thus substantiating the grounds for the principles of the present invention. Thereafter, an embodiment of the present invention will be described.

1. Outline of the Experiment

First, an experiment of acquiring a "disappointment signal", performed by the inventors, will be described. Then, it will be illustrated how it is possible to determine what in the presented information the user was paying attention to.

In the experiment, tests were conducted where a corresponding left-click or right-click was selected in accordance with a character of "L" or "R" displayed on the screen, and the operation result was confirmed with the expectation that "○" would be presented. While the test subject would expect "○", which indicates a result of correct selection, the test subject's expected operation would not occur with respect to "X", which is displayed with a probability of 20%. Only in this case was the latency confirmed to appear near 600 milliseconds.

A "latency" refers to a period of time until a positive peak is observed in an event-related potential of a user, since a starting point which is the point in time at which an operation result was presented by the appliance. As used herein, a "positive peak" means a peak at which a measured event-related potential takes a positive maximum value. However, it may not be limited to a positive maximum value. For example, it may be possible that, due to the influence of a noise elimination during the measurement, the waveform of the event-related potential may steeply drop in the negative direction at a certain place. In such a case, the waveform may be corrected based on the values therebefore and thereafter, and if the corrected value at the place of drop has a positive maximum value, that place may be treated as a positive peak.

Not only confirming the expected operation content based on simple identifiers such as "○" and "X", the inventors have also performed an experiment of confirming the operation content based on more complicated criteria. For example, an experiment was performed to confirm that a similar characteristic feature in the event-related potential also appears in an interface manipulation of an actual appliance, e.g., in a manipulation of selecting a video to watch on television.

Furthermore, the experiment measured an event-related potential of the user not only when confirming the expectation operation based on a simple identifier such as a channel number that is displayed in a corner of a content, but also when comparing the content which was expected by the test subject in selecting an action based on a genre name or program title against a video which was actually presented to the test subject and determining whether the content was as expected or not.

2. Details of the Experiment

Figure 9:
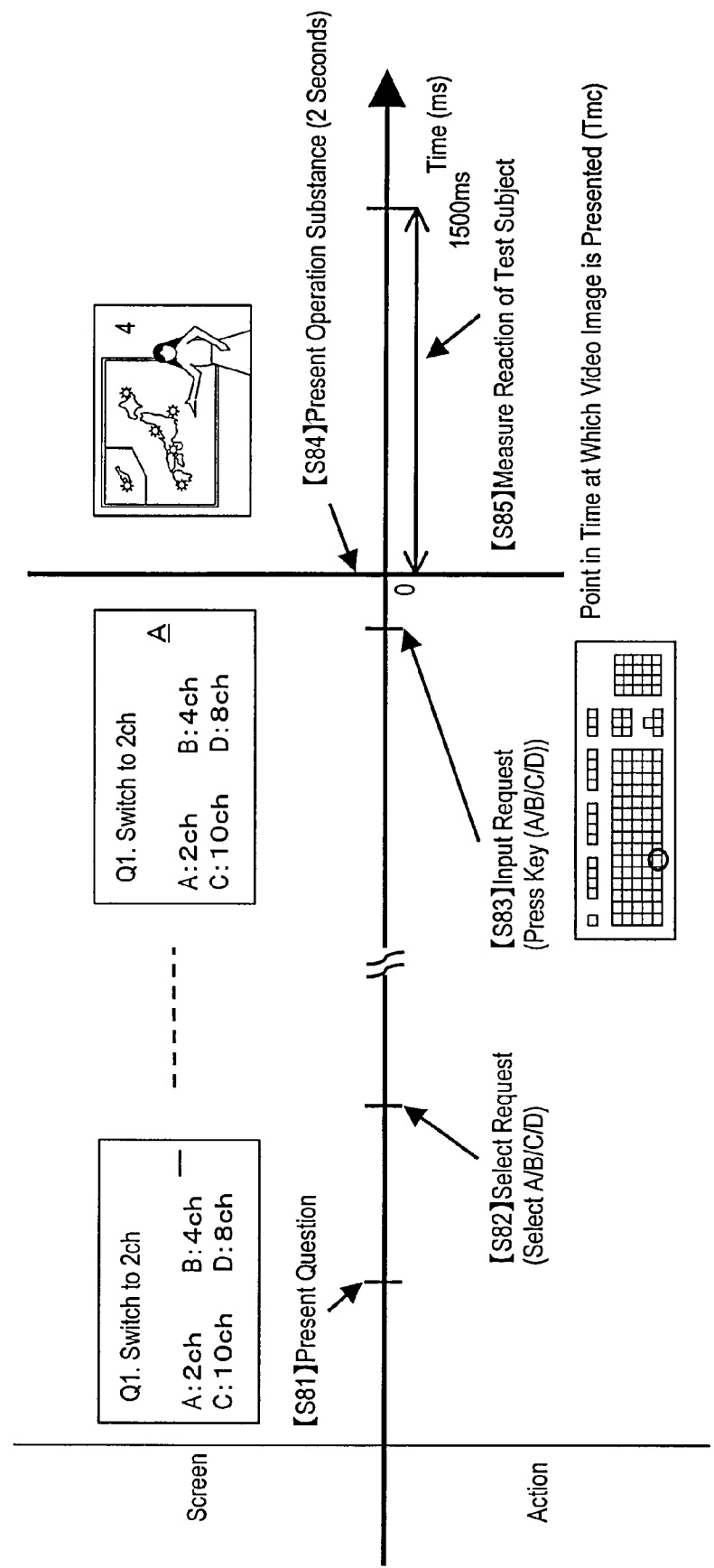
FIG. 9 A diagram showing an outline of the present experiment in chronological order.
Figure 11:
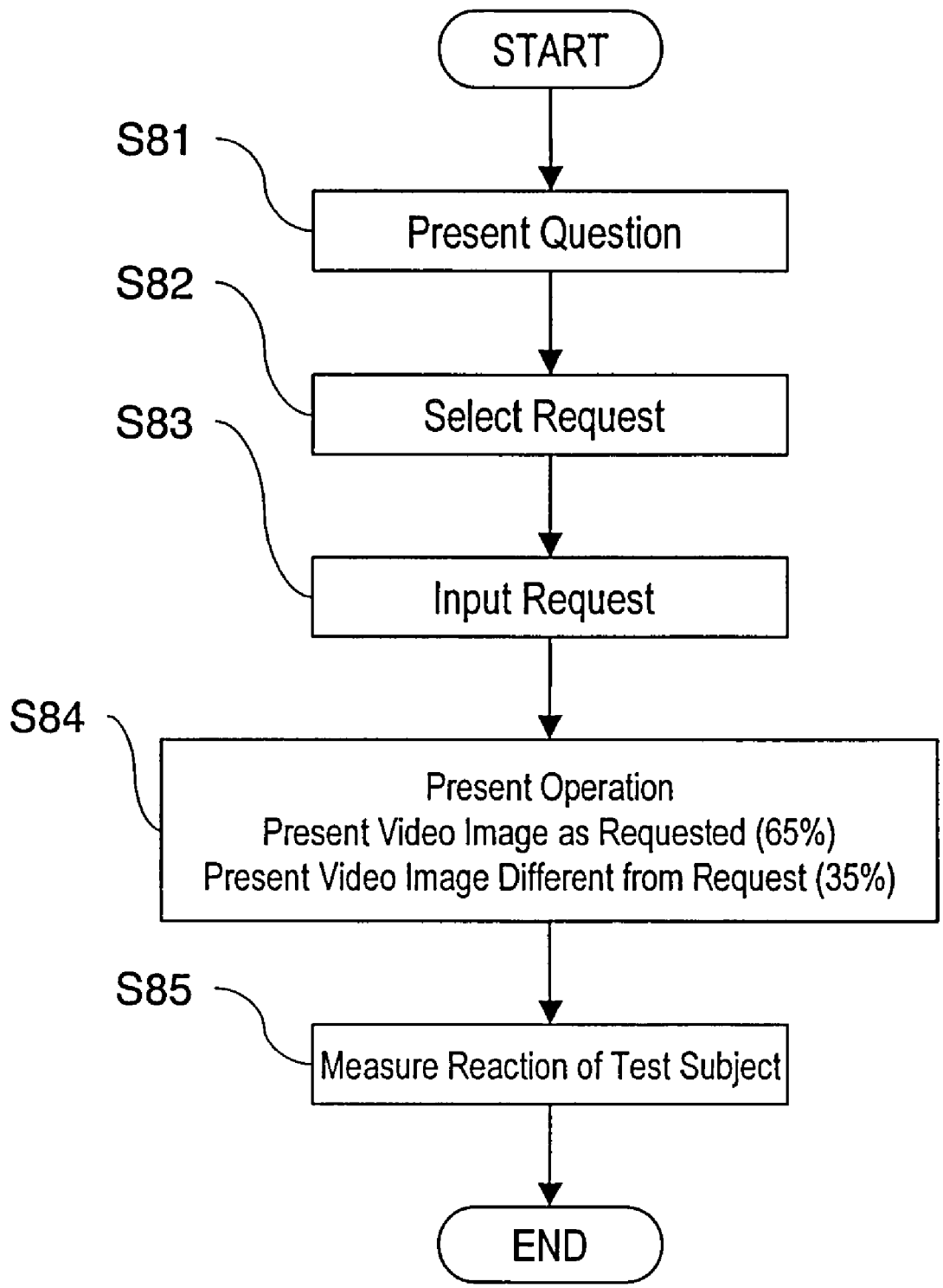
FIG. 11 A flowchart showing the procedure of the experiment.

FIG. 9 shows an outline of the present experiment in chronological order. FIG. 10 shows example questions used in the experiment. FIG. 11 shows the procedure of the experiment. With reference thereto, the body of the present experiment will be described below. Note that the descriptions of S81 to S85 shown in FIG. 9 correspond to the descriptions of S81 to S85 shown in FIG. 11.

In the present experiment, as shown in FIG. 9, an action for a question that is presented on a display (step S81) is selected from among four alternatives (step S82), and the selected alternative is input by a test subject to an appliance as his or her own request for the action via a keyboard or the like (step S83). A video is consequently presented on the display (step S84), and the reaction of the test subject when determining whether the video presented on the display is identical with an intended content relative to the requested content is measured by an electroencephalograph (step S85).

Hereinafter, steps S81 to S85 shown in FIG. 11 are specifically described.

(Step S81: Presenting a Question)

As shown in FIG. 9, on the display, a question and alternative actions to the question are simultaneously displayed to the test subject. Herein, three types of questions were presented: "concerning a request based on an identifier (question type 1)" such as a channel No., e.g., "switch to 2ch"; "concerning a request of a program based on genres (question type 2)", e.g., "switch to baseball"; and "concerning the content of the program itself (question type 3)", e.g., "switch to news Z". There were four alternatives. For example, as shown in FIG. 9, with respect to a question of "switch to 2ch", "A: 2ch, B: 4ch, C: 10ch, D: 8ch", etc., might be displayed.

FIG. 10 shows examples of different questions according to different question types. In any of these questions, an evaluation of the displayed information will be made on a usual television screen. However, when different types of questions are given, i.e., question type 1 which focuses on an identifier such as channel No., question type 2 which focuses on the genre, and question type 3 which focuses on the program itself, the test subject will pay different kinds of attention to the displayed information, in accordance with each question.

(Step S82: Selecting a Request)

The test subject confirms the question and alternatives which are given at step S81, and selects an action for the question from among the alternatives. In the example of FIG. 9, the test subject will select action A in order to switch to 2ch.

(Step S83: Inputting a Request)

To the appliance, the test subject inputs the action selected at step S82. Specifically, a key input on the keyboard that corresponds to alternatives A to D is made. In the example of FIG. 9, key A on the keyboard will be pressed.

(Step S84: Presenting an Operation Content)

After 200 ms since the keyboard input of step S83, a "video which is in accordance with the content of the selected action" is presented with a probability of 65% on the display, or a "video of a different content from the content of the selected action" is presented with a probability of 35% on the display. Herein, the video is presented for 2 seconds; and the content of the video is changed for each test. After 0.5 seconds since the end of the presentation of the video, a next question is presented.

Now, specific examples of "presenting a video which is in accordance with the content of the selected action" and "presenting a video of a different content from the content of the selected action" will be described, each in reference to question types 1 to 3.

Question Type 1 (Concerning a Request Based on an Identifier)

"Presenting a video which is in accordance with the content of the selected action" means, for example, presenting a video which is indicated as 2ch when 2ch was input. "Presenting a video of a different content from the content of the selected action" means, although 2ch was selected for input, presenting a video which is indicated with a different channel No., e.g., 4ch. FIG. 9 shows an example where a video of 4ch is being presented to the test subject although 2ch was selected. The genre of the video is weather forecast.

Question Type 2 (Concerning a Request Based on Genres)

The genres are divided into four: "news", "baseball", "animation", and "weather forecast". "Presenting a video which is in accordance with the content of the selected action" means, for example, presenting a video of baseball in response to an input of the "baseball" genre. "Presenting a video of a different content from the content of the selected action" means, although the "baseball" genre was selected for input, presenting a video of a different genre, such as "news", "animation", or "weather forecast".

Question Type 3 (Concerning the Content Itself)

As news programs, three programs of the following program titles are used: "news X", "news Y", and "news Z". "Presenting a video which is in accordance with the content of the selected action" means, for example, presenting a video of "news X" in response to an input of the program title of "news X". "Presenting a video of a different content from the content of the selected action" means, although the program title "news X" was selected for input, presenting a video of a different program, such as "news Y" or "news Z".

It is considered that the following differences in cognitive complexity exist among the aforementioned question types 1 to 3. A question of question type 1 involves perceiving differences between symbols such as 2ch and 4ch, and thus constitutes a relatively easy category. A question of question type 2 is a question of genre-level distinction, and requires perception of a video which is composed not only of symbols but also of diagrams, objects, and the like, the perception being made for different genres such as news, animation, or baseball. This type of question is considered as easy to perceive as in the case of symbol differences, because the color tone of a video clearly differs between an animation and anything else, and videos of a weather map, a ballpark, a news studio are clearly different. Differentiating categories per se can be said to be relatively easy.

On the other hand, a question of question type 3 is a question where videos of the same genre are to be further distinguished by their contents. For example, in order to distinguish between a plurality of videos belonging to the news genre by relying on the contents of the programs, it would be necessary to consider more subtle features such as the shape of the studio, the newscasters included, the subtitles, and the like. Furthermore, in the example of baseball, in order to further distinguish the program content such as "○ ○ VS X X", similarly subtle features such as different ballparks and different uniforms would need to be considered to enable perception. In other words, there are clearly different levels of cognitive complexity between question type 2, where only apparent differences between a ballpark and a weather map require distinction, and question type 3, where a distinction must be made between very similar things, e.g., as to which ballpark or which team's uniform.

Thus, in the present experiment, questions with different levels of cognitive complexity are presented to the test subject. By using the same presentation image for different question types, instead of examining reactions of the test subject merely in relation to changes of images, it becomes possible to examine the reactions of the test subject when there exist different levels of cognitive complexity concerning which content the test subject pays attention to in requests such as question types 1 to 3.

For example, even when using the same weather forecast image as that shown in FIG. 9, the question might be changed to "switch to baseball" to arouse an expectation involving a cognitive complexity at the genre level, or the question might be changed to "switch to 'weather forecast at X o'clock'" to arouse an expectation involving a cognitive complexity at the program content level. By asking a mixture of such questions, instead of examining reactions of the test subject merely in relation to changes of images, it becomes possible to examine the reactions of the user in respect of comparisons between a presented content and expected contents involving different levels of cognitive complexity concerning different request contents.

(Step S85: Measuring a Reaction of the Test Subject)

By defining the time at which a video is presented at step S83 as a starting point, an event-related potential of the electroencephalograms of the test subject is measured.

Two experiments were performed for each test subject, where each experiment comprised 120 tests according to the procedure of FIG. 11. Thus, data of a total of 240 tests was measured with respect to each test subject.

Figure 12:
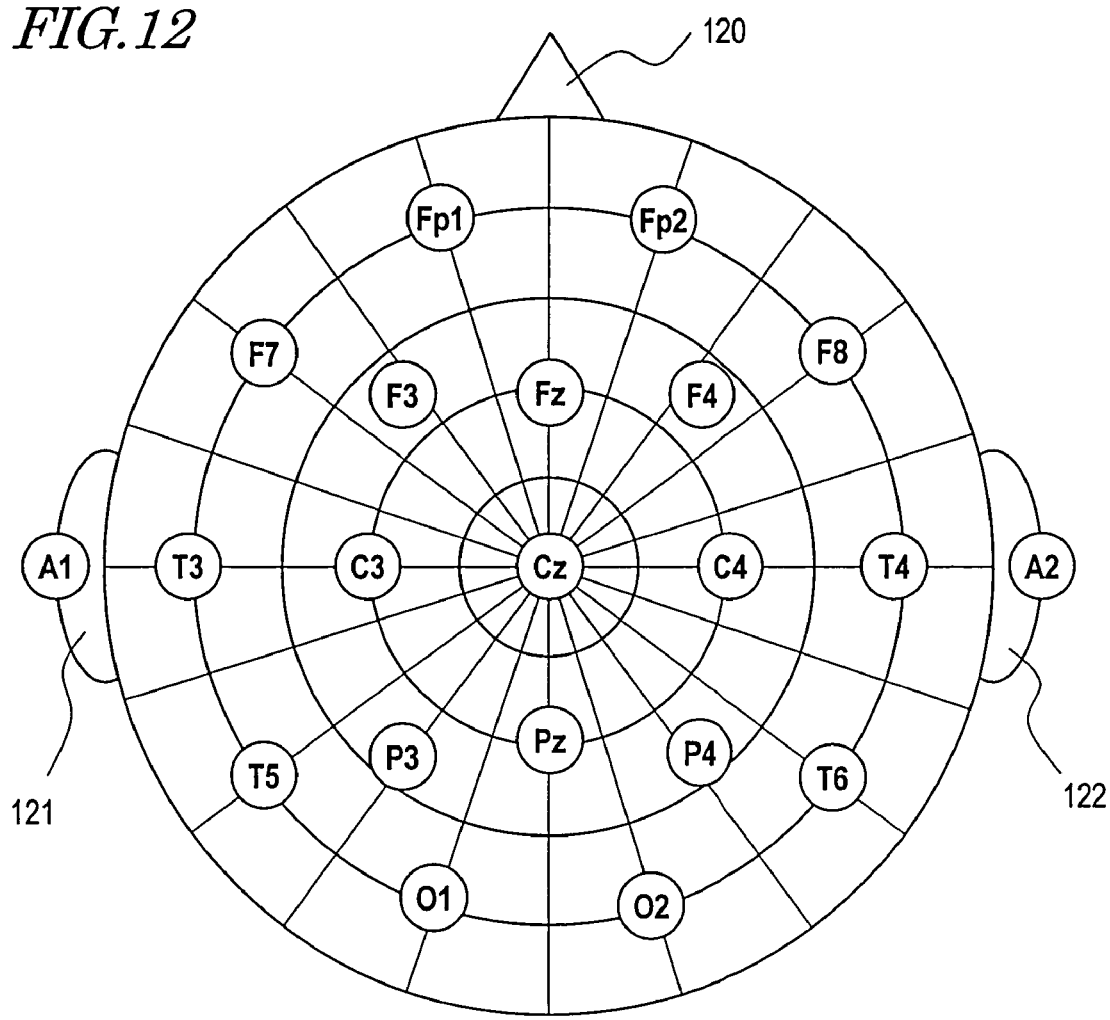
FIG. 12 A diagram showing positions at which electrodes for measuring electroencephalograms of a test subject are attached.

FIG. 12 shows positions at which electrodes for measuring the electroencephalograms of a test subject are attached. These attachment positions comply with the International 10-20 system. As an aid for clarifying the positional relationship, a nose 120, a left ear 121, and a right ear 122 of the test subject are shown in FIG. 12. In FIG. 12, any electrode that is on a median line which is equidistant from the left ear 121 and the right ear 122 and passes through the nose 120 is labeled as "z".

The electrodes for measuring the event-related potential were attached at 4 places, namely, 1) Pz: median vertex, 2) 3) A1, A2: both earlobes, 4) body ground, and (Z): root of nose. The sampling frequency was 200 Hz.

In the analysis of the experimental data, a 0.05-10 Hz band-pass filter was used, and a waveform from 200 ms to 0 ms before the stimulation was used for baseline correction. Moreover, in the present experiment, in order to eliminate noises associated with blinks, an electrooculogram (EOG) was simultaneously measured, and any test resulting in an EOG component having an amplitude of 100 μV or more was deleted from the data subjected to analysis.

FIGS. 13($a$) to ($c$) are graphs showing analysis results of experimental data for question types 1 to 3, respectively. The waveform in each of the graphs of FIGS. 13($a$) to ($c$) is obtained by accumulating the potential waveforms obtained from three test subjects, where the horizontal axis represents the time since the presentation of a video (unit: ms) and the vertical axis represents the potential (unit: μV). Thick lines 31, 33, and 35 each represent a waveform when a video which is unrelated to an input request (selected action) is presented, whereas thin lines 32, 34, and 36 each represent a waveform when a video which is related to an input request (selected action) is presented.

From the graphs of FIG. 13($a$) and FIG. 13($b$), it can be seen that, when a video which is unrelated to the input request (selected action) is presented (e.g., a video which is indicated as 4ch being presented for an input of 2ch in the case of FIG. 13($a$), or a video of a weather forecast being presented for an input of the baseball genre in the case of FIG. 13($b$)), an event-related potential having a characteristic feature which is different from usual appears around 600 milliseconds since the presentation of the video. This indicates that, in an actual appliance manipulation, a clear difference is observed in the event-related potential that is measured by an electroencephalograph, between the case where the appliance has operated as expected by the user and the case where the appliance has not operated as expected by the user.

Moreover, in the graph of FIG. 13(c), a difference is observed in the neighborhood of 750 milliseconds since the presentation of the video, between the waveform 35 when a video which is unrelated to an input request (selected action) is presented (e.g., a video of "news Z" being displayed for an input of "news X") and the waveform 36 when a video which is related to the input request (selected action) is presented (e.g., a video of "news X" being displayed for an input of "news X"). Also in this case, in an actual appliance manipulation, a clear difference exists in the event-related potential that is measured by an electroencephalograph, between the case where the appliance has operated as expected by the user and the case where the appliance has not operated as expected by the user. In the case where the focus is on the program title instead of the genre, a characteristic feature is observed that has a positive peak near 750 milliseconds, as opposed to the aforementioned 600 milliseconds.

Thus, depending on what the test subject has been paying attention to, a difference results in the detected waveform, and more specifically the latency. The difference in the latency is ascribable to a difference in the time required in determining whether the information to which attention has been paid turns out as expected or not. Considered in reverse, regarding the same disappointed state, it is possible in a detected waveform to detect what the test subject has been paying attention to in arriving at the state of disappointment, by relying on the difference in latency.

A majority of conventional experiments on event-related potentials have examined reactions to simple visual input or aural inputs. In such experiments, latency may be observed around 300 to 450 milliseconds.

Under the condition where a television screen is utilized as in the experiment performed by the inventors, it is considered that the latency shift to: near 600 milliseconds for the discrimination of differences in the channel No. or genre, which pertain to question types 1 and 2 (relatively easy discrimination); or near 750 milliseconds for the discrimination of differences in the program title only, within the same genre, which pertain to question type 3 (complicated discrimination). Note that, in the present experiment, as in the aforementioned experiment, it is presumable that the time at which a peak appears may differ from individual to individual, and from test to test.

Thus, as is clarified by this experiment, a clear difference exists in the event-related potential which is measured by an electroencephalograph, between the case where the appliance has operated as expected by the user and the case where the appliance has not operated as expected by the user. Furthermore, the latency in the event-related potential also changes depending on what the user has been paying attention to. Through this experiment, it is possible to detect what the user has been paying attention to in the interface of the appliance, by using this event-related potential. This is to say that it is possible to determine whether the displayed information has caused a disappointment within the same genre, or a disappointment in a different genre.

3. Construction of the System According to the Present Embodiment

Hereinafter, an embodiment of an information processing system according to the present invention will be described. The information processing system is used in detecting what the user's attention is directed to and in making a response which is closer to the user's expectation. Therefore, the information processing system can be called an "attention detection system".

First, with reference to FIG. 1, a specific example of the attention detection system will be described, and with reference to FIG. 2 to FIG. 8, the generic construction and operations of the attention detection system will be described.

FIG. 1 shows an exemplary construction of an attention detection system 100 according to the present embodiment. The attention detection system 100 includes an attention detection device 1, a remote control 11-1, a microphone 11-2, a TV 14-1, loudspeakers 14-2, and a biological signal detection section 15.

The functions of the attention detection system 100 will be generally described. The attention detection device 1 comprised in the attention detection system 100 receives a request from the user 10 via the remote control 11-1 or the microphone 11-2. Then, in response to this request, it performs processes for outputting video/audio.

For example, if a user's request that "I want to watch television" is wirelessly input via the microphone 11-2, the attention detection device 1 performs a process for sending a power-on instruction to the television set, and also performs a process of receiving broadcast waves and a tuning process. Furthermore, it performs an outputting process with respect to a video signal and an audio signal separately. As a result, the TV 14-1 displays a video of the program based on the video signal, and the loudspeakers 14-2 output an audio of the program based on the audio signal.

Next, the attention detection device 1 acquires a brain-wave signal from the biological signal detection section 15. The biological signal detection section 15 of the present embodiment is contemplated as a head-mount type electroencephalograph, and is capable of wirelessly transmitting a detected brain-wave signal to the attention detection device 1. Note that this electroencephalograph has electrodes placed thereon, such that, when worn on the head of the user 10, the electrodes will come in contact with predetermined positions on the head.

In the case where an electrode placement similar to the conditions of the already-described experiment of acquiring a "disappointment signal" is adopted, the electrodes are placed at Pz (median parietal), A1,A2 (both earlobes), and the nasion of the user 10, as shown in FIG. 12. However, it suffices if there are at least two electrodes, and potential measurements can be made with Pz and A1 alone, for example. The electrode positions are to be determined in terms of reliability of signal measurement, ease of wearing, and the like. As a result, the biological signal detection section 15 is able to measure an event-related potential of the user 10.

The attention detection device 1 analyzes the received brain-wave signal to determine whether the user 10 has felt disappointment towards the output result or not.

If a disappointment is determined, an event-related potential signal is further extracted from within the brain-wave signal, and an elapsed time since a video was presented by the apparatus (latency) is identified. Then, it is determined whether the latency is closer to 600±50 milliseconds, or 750±50 milliseconds.

If the latency is 600±50 milliseconds, it means that the presented program is an obvious disappointment. Therefore, the attention detection device 1 tunes to and displays another program which belongs to a different category from that of the current program. On the other hand, if the latency is 750±50 milliseconds, it means that the presented program is relatively close to the desired program but still is a disappointment. Therefore, the attention detection device 1 tunes to and displays another program which belongs to the same category as that of the program which is currently being displayed. As a result, a more appropriate program can be outputted in accordance with the degree of disappointment of the user.

Note that the attention detection device 1 retains a program database of a plurality of parameters such as channel Nos., genres, program titles, viewing history, etc., of programs. The attention detection device 1 is able to classify a plurality of broadcast programs into categories based on genres, for example, and easily select programs in different categories.

4. Detailed Construction of the System of the Present Embodiment

FIG. 2 shows a functional block construction of the attention detection system 100. FIG. 2 also shows the detailed functional blocks of the attention detection device 1. The user 10 block is illustrated for convenience of explanation.

The attention detection device 1 is connected to the input section 11, the output section 14, and the biological signal detection section 15 in a wired or wireless manner, and performs transmission and reception of signals. Although FIG. 2 illustrates the input section 11, the output section 14, and the biological signal detection section 15 as separate entities from the attention detection device 1, this is only exemplary. Some or all of the input section 11, the output section 14, and the biological signal detection section 15 may be provided within the attention detection device 1.

The input section 11 is a device which is manipulated by the user 10 to input an instruction to the attention detection device 1. The input section 11 corresponds to the remote control 11-1 and the microphone 11-2 in FIG. 1. A mouse, a keyboard, a camera, a gyro sensor, an acceleration sensor, and the like may also be included.

The output section 14 is a device which receives a signal from the attention detection device 1, and outputs a content which is based on that signal. The output section 14 corresponds to the TV 14-1 and the loudspeakers 14-2 in FIG. 1. The output section 14 can also output text characters, synthetic voices, and the like. What is output is not limited to a video or audio. For example, an operation of an actuator, etc., may also be encompassed as an output.

The biological signal detection section 15 is an electroencephalograph which detects a biological signal from the user.

Next, the detailed construction of the attention detection device 1 will be described.

The attention detection device 1 is implemented as a computer system which executes the subsequently-described processes. The attention detection device 1 includes a central processing unit (CPU) 2, a RAM 3, a computer program 4, and a storage section 5.

By executing the computer program 4 stored in the RAM 3, the CPU 2 realizes functions in accordance with the processing procedure of the program. In the present embodiment, the CPU 2 realizes three main functions, namely:

(1) an appliance reaction function of determining a reaction (output content) of the attention detection device 1 based on the user's request, and executing processes;

(2) a signal analysis function of analyzing a biological signal which is detected by the biological signal detection section 15 and extracting information to be focused on; and (3) a reaction modification function of modifying the reaction of the attention detection device 1 based on the signal which has been analyzed by the signal analysis section 16 and prospective operation modifications which are stored in the storage section 13. In the present specification, the functions of (1) to (3) are realized by separate programs. However, they can be realized in the form of different processing modules, etc., which are within a single program. The computer program is recorded on a storage medium, e.g., a CD-ROM, which is readable by a computer. Then, it is distributed on the market as a computer program product, for example, or transmitted through telecommunications lines, e.g., the Internet.

In FIG. 2, functions corresponding to (1) to (3) above are regarded as component elements of the attention detection device 1, and illustrated as the appliance reaction section 12, the signal analysis section 16, and the reaction modifying section 17, respectively. As mentioned earlier, they may be realized by software means, but may also be realized by hardware means, e.g., DSPs.

The storage section 5 is a hard disk drive, for example. The storage section 5 retains a database to be used when the appliance reaction section 12 determines a reaction, and also stores the information on prospective operations of the appliance, which is generated by utilizing the database.

It is assumed that the attention detection system 100 of the present embodiment is to be used in an environment where the user views a broadcast program. Under such an assumption, the storage section 5 retains a program database concerning broadcast programs.

Figure 3:
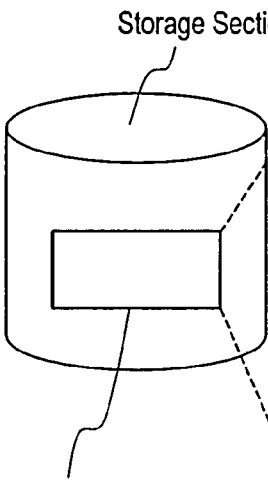
FIG. 3 A diagram showing an example of a program database 51 which is retained in a storage section 5.

FIG. 3 shows an example of a program database 51 which is retained in the storage section 5. Each row in the program database 51 corresponds to program information of each program. One piece of program information is composed of a channel No. parameter 52, a genre parameter 53, a program title parameter 54, and a viewing history parameter 55. In these parameters, information representing a channel No., a genre, a program title, and a viewing history, respectively, of the program are described.

Any information other than the viewing history is generated from program guide information. Program guide information is, for example, information which is utilized for generating an electronic program guide. The attention detection device 1 can acquire program guide information via broadcast waves or a communication network. On the other hand, information of a viewing history indicates the time(s) and date(s) when the user viewed that program. The number of entries in the viewing history of each program represents the frequency of viewing (number of times) of the program.

5. Processes by the Attention Detection System 100

Figure 4:
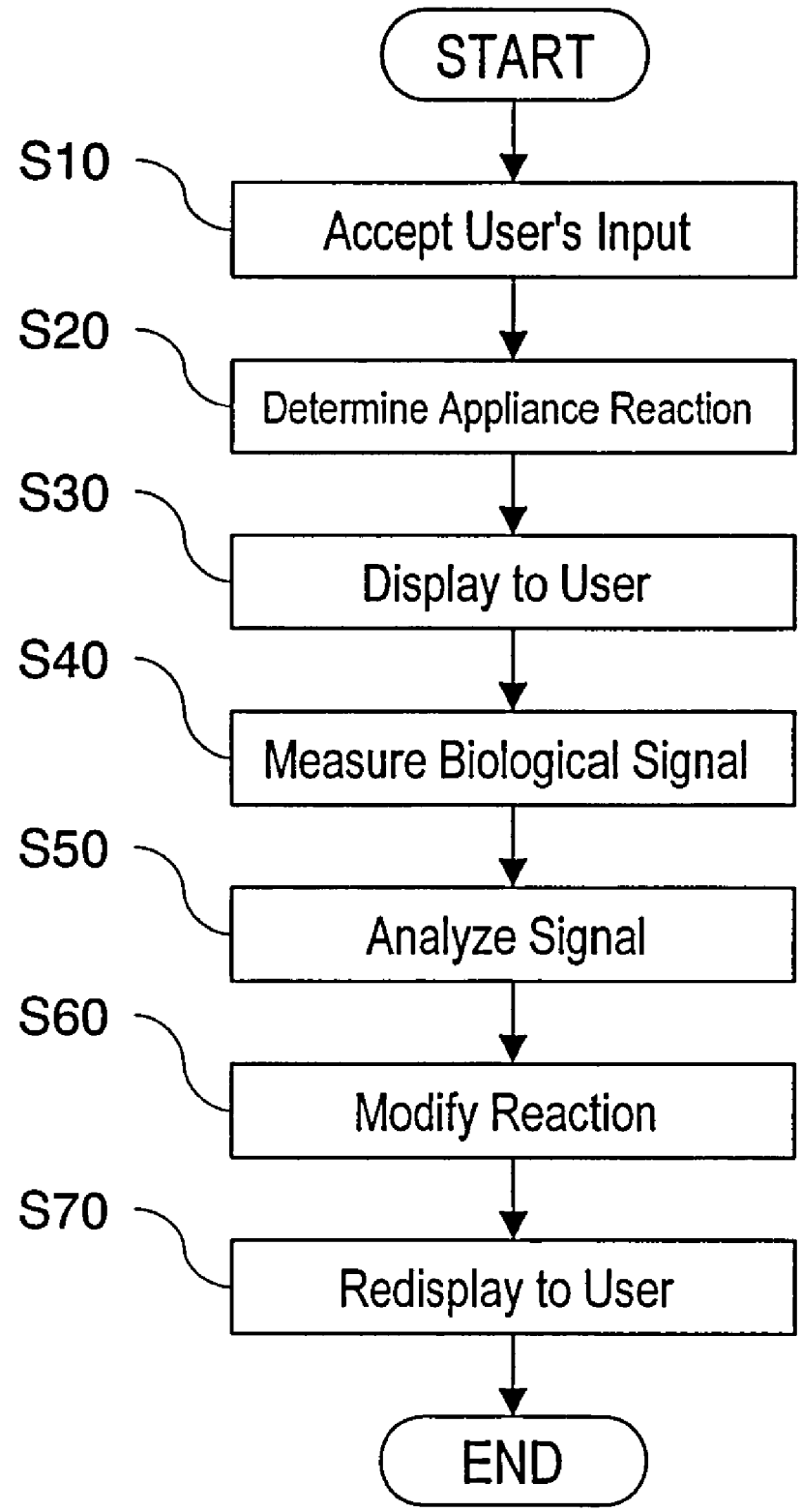
FIG. 4 A flowchart showing the procedure of processes by the attention detection system 100.

Next, with reference to a flowchart of FIG. 4, a flow of the overall processing by the attention detection system 100 of FIG. 2 will be described. FIG. 4 shows the procedure of processes by the attention detection system 100.

At step S10, the input section 11 accepts an input of a request from the user 10. For example, the input section 11 accepts an input to "Turn on the TV" from the user.

At step S20, based on the input result, the appliance reaction section 12 determines the content of an output to the user 10. The output content is to be determined so as to best suit the request of the user 10. If the request of the user 10 is not clear enough, the attention detection device 1 must guess the request of the user 10. By referring to the program database 51 (FIG. 3) retained in the storage section 5, the appliance reaction section 12 decides to tune to a program that has a most frequent viewing history among the programs which are being broadcast at that point in time.

At step S30, the output section 14 presents the determined output content. Herein, a video and an audio of the program that has been tuned to are output.

At the next step S40, the biological signal detection section 15 measures a biological signal from the user 10. In the present invention, changes in the brain potential that are measurable by an electroencephalograph are recorded. The measurement method is similar to the measurement method in the already-described experiment.

At step S50, the signal analysis section 16 analyzes the biological signal which has been measured. More specifically, the signal analysis section 16 pays attention to an electroencephalogram event-related potential in the biological signal to determine whether a specific electroencephalogram event-related potential waveform is contained in the signal or not.

At step S60, the reaction modifying section 17 determines whether or not to modify the output content based on the signal analysis result, and if modification is necessary, modifies the output content. Specifically, if it is determined based on the analyzed biological signal that there is no problem with the output content (i.e., the program being displayed), the reaction modifying section 17 does not perform modification. On the other hand, if it is determined that the output content is not in accordance with the user's expectation, the reaction modifying section 17 modifies the output content. In this case, it is decided to tune to a program which is the next candidate.

Then, at step S70, the appliance reaction section 12 again presents a content via the output section 14, based on the result of the process of step S60.

According to the above processes, if the output result of the attention detection device 1 is not in accordance with the user's expectation, the attention detection device 1 can modify its output content without the user 10 having to explicitly indicate his or her will. Therefore, a smooth interaction occurs between the user 10 and the attention detection device 1.

Hereinafter, with reference to FIG. 5 to FIG. 8, the processes of steps S20, S50, and S60 above will be specifically described.

6. Processes by the Appliance Reaction Section

First, with reference to a flowchart of FIG. 5, the process of step S20 in FIG. 4 will be specifically described. This process is performed by the appliance reaction section 12.

FIG. 5 shows the procedure processes by the appliance reaction section 12.

At step S21, the appliance reaction section 12 analyzes the content of the input from the user 10. Then, the appliance reaction section 12 finds an association between the request of the user 10 and a corresponding one of the services which can be provided by the attention detection device 1.

In the analysis, a speech recognition program or parsing program may be used for an audio input, for example. An image recognition program may be used for a gesture input. As for a mouse or keyboard input, an input/output program may recognize which key has been pressed, etc.

At step S22, a list of prospective operations is made. Generally speaking, an input from the user 10 needs to be recognized in the process performed at step S21. However, it is difficult to completely understand the request.

For example, it is difficult for a speech recognition program to recognize all of the user's speech. Even assuming an adequate performance of the speech recognition program, if the sentence uttered by the user 10 contains some ambiguity, it may be insufficient as an instruction for an operation of the attention detection device 1. In such a case, there will be a number of prospective operations.

As for a request to "Turn on the TV", the request to power ON the television set is easy to interpret. However, there is no instruction as to which program may be first displayed after powering ON the television set. Therefore, it is necessary to determine which program (content) is to be displayed first.

Accordingly, in the present embodiment, the appliance reaction section 12 creates a list of prospective operations among those which have experienced a high frequency of viewing by the user 10. Specifically, the appliance reaction section 12 creates a list of prospective operations by placing them in a descending order of frequency of viewing, based on the number of instances in the viewing history information of the program database 51. By thus determining the prospective operations, the attention detection device 1 can operate in accordance with the user's expectation as much as possible.

FIG. 6 shows a list 41 of prospective operations that has been created by the appliance reaction section 12. Among the programs which are viewable at the time when the request is input, the appliance reaction section 12 arranges the information of those programs having high frequencies of viewing in order. As for programs which have experienced the same number of instances, a rule may be defined that the program which has been viewed more recently is given a higher place, for example. Such an order can be seen as representing a descending order of reliability among the prospective operations.

From the list 41 of prospective operations, it can be seen that a program "news X" has been placed the first among the prospective operations, based on the timing when the user 10 made requests and the viewing history so far. This is followed by a program "news Y" ranking the second, a program "weather forecast C" ranking the third, and a program "animation A" ranking the fourth. They all satisfy the request to "Turn on the TV", but it is presumable that only one of them is what the user 10 really wants.

Moreover, in connection with the operation which is adopted as ranking the first among the prospective operations, prospective operations belonging to the same category and prospective operations belonging to different categories are indicated by the "same:" symbol and the "different:" symbol, respectively. These categories are determined based on the genres of the programs, and are described in the genre parameter 53 shown in FIG. 3.

For example, since the "news Y" ranking the second belongs to the same news category as the "news X" ranking the first, "same:" is assigned to the "news Y". On the other hand, the "weather forecast C" ranking the third and the "animation A" the ranking the fourth are not news, and therefore "different:" is assigned to them. The inventors have found that such identicalness/non-identicalness between categories can be detected based on the event-related potential of the electroencephalogram. Therefore, information concerning categories is included as a criterion for choosing a next candidate.

Note that FIG. 6 also shows lists 42 and 43 concerning other requests. The list 42 shows prospective operations with respect to a request that "I want to watch baseball". With respect to the request of wanting to watch baseball, all of the prospective operations satisfy the request sentence. However, the degree of user disappointment greatly differs between the case of wanting to watch a professional baseball or major league video which is broadcast as a television program and the case of wanting to watch a video of a previous game of a sandlot baseball team to which the user himself or herself belongs.

The list 43 shows prospective operations with respect to a request to "Get me that", directed to a robot having an actuator or the like. The latter list is an example of a request and list in a system which is different from the example shown in FIG. 1. When the user 10 wants the robot to get a newspaper, there will be no particular problem if processes for performing the prospective operation ranking the first (moving process, picking up process, etc.) are executed. However, if something other than a newspaper was being desired, the degree of user disappointment will greatly vary depending on whether it was glasses or mail that was being desired.

FIG. 5 is again referred to. At step S23, the appliance reaction section 12 stores the resultant list of prospective operations to the storage section 13. This list of prospective operations will serve as the data to be considered when outputting an operation in the case where the information presented to the user 10 is not as expected by the user 10 (described later).

At step S24, in the current list of prospective operations stored in step S23, the appliance reaction section 12 selects a candidate having the highest reliability, and determines it as an output operation. In the case where a plurality of prospective operations are determined, some sort of certainty criterion for the inference operation are to be determined. Generally referred to as a reliability, etc., this is assigned to each prospective operation in the calculation of prospective operations. For example, it is set based on the past frequencies of operation selection, profile information, or the like of the user 10, and a candidate having the highest value of this is output.

In usual conversations which the user may hold with other humans, there may be speeches which contain ambiguity such that the content of the speeches can only be identified in reference to the past context or the like. Being able to correctly interpret these in attending the user is an indispensable function of an attention detection device 1 or robot which is to be used in an amicable relationship with the user.

Thus, through the above-described processes, the attention detection device 1 is able to operate in accordance with the user's expectation as much as possible, upon receiving a request of the user 10. However, the prospective operation that was first adopted may not necessarily be in accordance with the user's expectation. In such a case, being able to quickly modify to a proper operation will also be an effective function. This is why the processes steps S50 and S60 in FIG. 4 are needed.

7. Processes by the Signal Analysis Section

Figure 7:
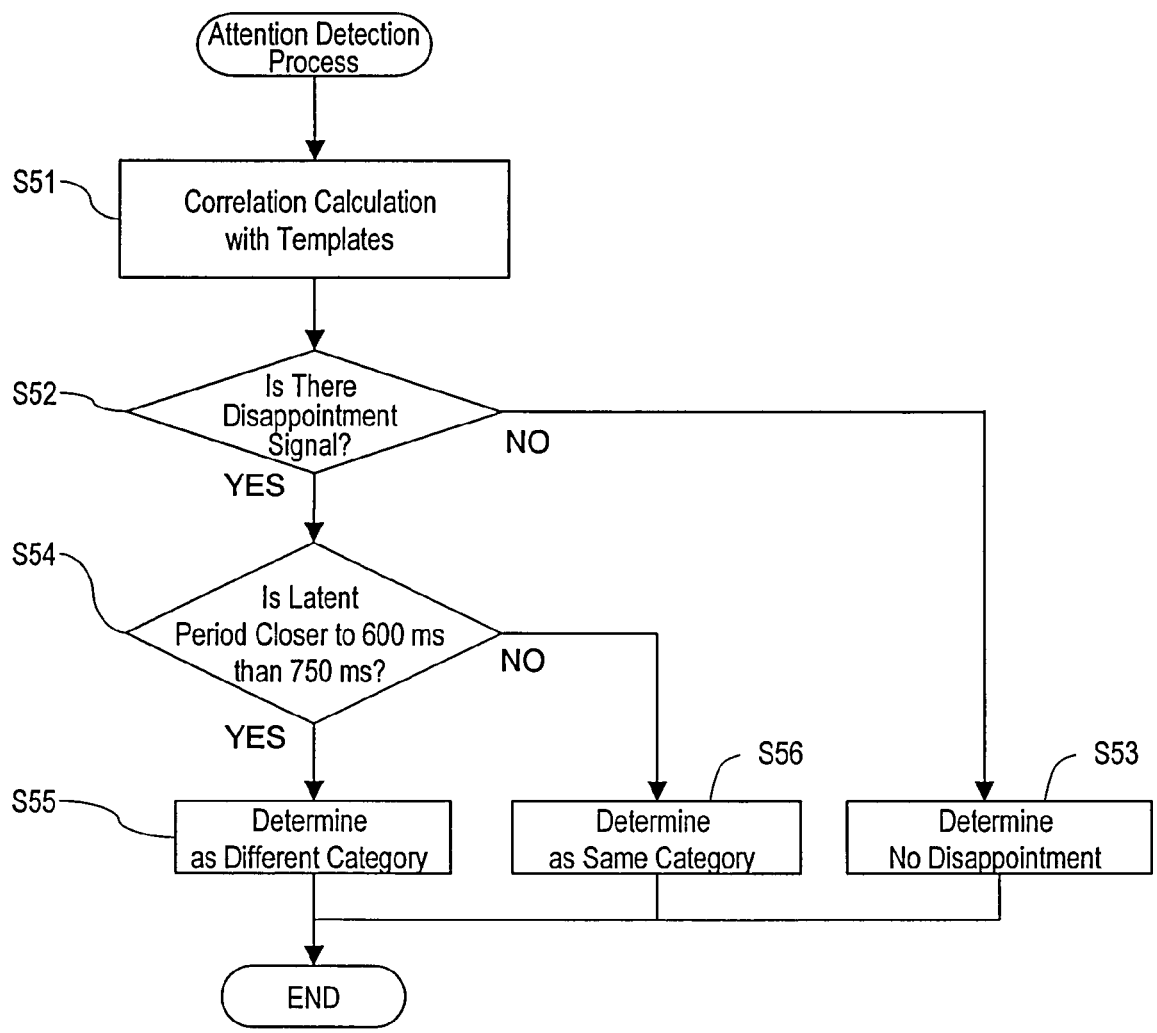
FIG. 7 A flowchart showing the procedure of processes by a signal analysis section 16.

Next, with reference to a flowchart of FIG. 7, the process of step S50 in FIG. 4 will be specifically described. This process is performed by the signal analysis section 16.

FIG. 7 shows the procedure of processes by the signal analysis section 16.

At step S51, the signal analysis section 16 performs a correlation calculation between the acquired brain-wave signal and templates, and calculates which template the current waveform is more correlated to.

A template is a typical waveform of a state to be distinguished. Two templates, i.e., a template of a waveform when the user is in a disappointed state and a template of a waveform when the user is not in a disappointed state are prepared through previous experiments or the like. For example, they can be created from an average of the waveforms of each state. Then, the respective data are stored in the storage section 5.

Through the correlation calculation, it can be determined whether the user is in a disappointed state or not. Note that methods of correlation calculation are well-known. For example, the signal analysis section 16 may perform the correlation calculation by utilizing a process which performs discrimination by using a discrimination ratio, utilizing the Mahalanobis distance which is described in FIG. 8 of Patent Document 1. Detailed descriptions thereof are omitted in the present specification.

At step S52, the signal analysis section 16 switches the process depending on the size of the correlation value calculated at step S51. If there is a higher correlation with the template for disappointment, the signal analysis section 16 determines that a disappointment signal is contained, and the process proceeds to step S54. On the other hand, if there is a higher correlation with the template for non-disappointment, the signal analysis section 16 determines that no disappointment signal is contained, and the process proceeds to step S53.

At step S53, the signal analysis section 16 determines that no disappointment signal is contained, and this attention detection process is ended.

At step S54, the signal analysis section 16 identifies a positive peak in the event-related potential based on the detected electroencephalograms waveform, and calculates the time (latency) from a starting point until such a peak is observed, the starting point being the point in time when the program is displayed. As already described, the latency can serve as a signal for determining a degree of discrepancy from the expectation of the user 10. Then, if the calculated latency is closer to 600 milliseconds than 750 milliseconds, the process proceeds to step S55, and otherwise proceeds to step S56. Note that 600 milliseconds and 750 milliseconds do not need to be exact values. In view of individual differences and the like, it would be preferable to allow for a tolerance of about +50 milliseconds for each.

At step S55, the signal analysis section 16 determines that the category of the program being displayed differs from the category of the program expected by the user 10. Then, the attention detection process is ended.

At step S56, the signal analysis section 16 determines that the category of the program being displayed matches the category of the program expected by the user 10, but they are of different contents (programs). Then, the attention detection process is ended.

By performing such a process, the electroencephalograms of the user 10 can be categorized, and it is possible to determine whether the user 10 is currently feeling a disappointment with the output of the attention detection device 1, and if there is a disappointment, determine the degree of disappointment. This process can be said to be a process of determining which aspect of the information the user has been paying attention to. Therefore, the process of step S50 is called an attention detection process.

In the above embodiment, templates are used only as to the determination of presence or absence of a disappointment signal. Other than that, it might be possible to adopt a method in which three types of templates (a template when there is no disappointment; a template when there is a disappointment across different categories; and a template when there is a disappointment in the same category) are prepared, and determines which template the highest correlation exists with. In this case, by making the determinations of step S53, step S55, and step S56 with respect to each of the three types of templates, the same effect can be obtained.

8. Processes by the Reaction Modifying Section

Figure 8:
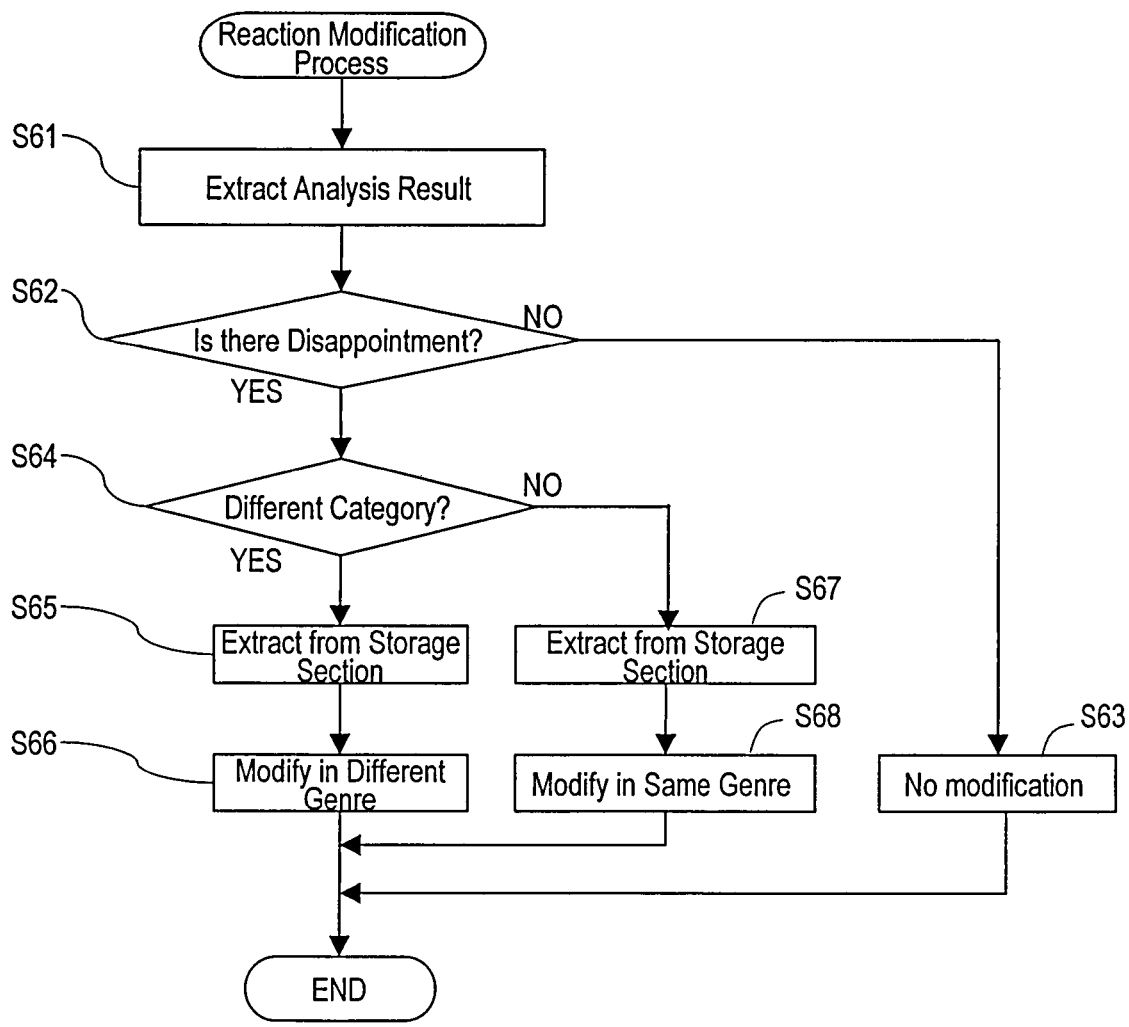
FIG. 8 A flowchart showing the procedure of processes by a reaction modifying section 17.

Next, with reference to a flowchart of FIG. 8, the process of step S60 in FIG. 4 will be specifically described. This process is performed by the reaction modifying section 17.

FIG. 8 shows the procedure of processes by the reaction modifying section 17.

At step S61, the result of the analysis performed by the signal analysis section 16 (step S50) is extracted. The analysis result means the result of the determination of step S54 in FIG. 7, i.e., the determination result of step S53, S55, or S56.

At step S62, the reaction modifying section 17 determines presence or absence of a disappointment. If the determination of no disappointment at step S53 in FIG. 7 has been made, the process proceeds to step S63. At step S63, the reaction modifying section 17 determines that the operation needs no modification, and ends the process.

At step S64, the reaction modifying section 17 determines whether or not the signal analysis section 16 has made a determination of a different category. If the different-category determination at step S55 in FIG. 7 has been made, the process proceeds to step S65. On the other hand, if the different-category determination has not been made, i.e., if the same-category determination of step S56 in FIG. 7 has been made, the process proceeds to step S67.

At step S65, the reaction modifying section 17 extracts the list 41 of prospective operations stored in the storage section 13, and executes the next step S66. Then at step S66, a program of a different genre is selected based on the prospective operation extracted at step S65, and it is decided to tune to the selected program.

With reference to the example of the list 41 of prospective operations shown in FIG. 6, when steps S65 and S66 are executed, it means that, regarding "news X" ranking the first among the prospective operations, the user 10 felt a disappointment with this appliance operation, and was expecting a program of a different category from that of "news X". Accordingly, the reaction modifying section 17 searches the list 41 of prospective operations for programs of different categories, sequentially from the higher priority side. Then, "weather forecast C" ranking the third is extracted as the tuning candidate. Then, at step S66, the current "news X" is modified to "weather forecast C".

Next, step S67 and step S68 are described. At step S67, the reaction modifying section 17 extracts the list 41 of prospective operations stored in the storage section 13, and executes the next step S68. At step S68, the reaction modifying section 17 selects a program of the same genre based on the prospective operation extracted at step S67, and decides to tune to the selected program.

With reference to the example of the list 41 of prospective operations shown in FIG. 6, when steps S67 and S68 are executed, it means that, regarding "news X" ranking the first among the prospective operations, the user 10 felt a disappointment with this appliance operation, and was expecting a program in the same category as that of "news X". Accordingly, the reaction modifying section 17 searches the list 41 of prospective operations for programs of the same category, sequentially from the higher priority side. Then, "news Y" ranking the second is extracted as the prospective operation. At step S68, the current "news X" is modified to "news Y". As a result, "news Y" is output, thus conforming to the user's expectation. Note that, since "news Y" is tuned to, the viewing history of the program database 51 is updated.

Through such a process, a disappointment signal from the user 10 is detected, and upon determining what has been paid attention to that caused the disappointment, the operation is modified. Thus, an operation is provided which comes as close to the expectation of the user 10 as possible.

With the aforementioned construction and operation of the attention detection system 100, the operation process to be next performed by the appliance is varied depending on whether a latency was measured in the neighborhood of 600 milliseconds or in the neighborhood of 750 milliseconds. If the latency was measured in the neighborhood of 600 milliseconds, the category itself was different from the user's expectation, and thus the appliance executes a process which is in a different category from the current operation process.

On the other hand, if the latency was measured in the neighborhood of 750 milliseconds, the category was the same but the content was different from the user's expectation, and thus the appliance executes a process which is in the same category as the current operation process. As a result, even if the appliance has not operated in accordance with the user's desire, the appliance is able to modify its operation according to the user's attention, without an explicit designation from the user.

Thus, an embodiment of the present invention has been described.

In FIG. 7 above, presence or absence of a disappointment signal is determined at step S52, and the time at which a latency is observed is determined at a subsequent step S54. However, these two steps may be unified. For example, three types of templates may be used at step S51: a template of a waveform in which a positive peak appears in the neighborhood of 600 milliseconds; a template of a waveform in which a positive peak appears in the neighborhood of 750 milliseconds; and a template of a waveform when the user is not in a disappointed state. Then, correlation calculations between the acquire brain-wave signal (event-related potential) and the three types of templates are performed. As a result, not only a result as to the presence or absence of disappointment, but also a result as to whether the latency is in the neighborhood of 600 milliseconds or in the neighborhood of 750 milliseconds can be simultaneously output.

At step S60 shown in FIG. 4, information that is directed to the user 10 at that point in time is modified. However, when next generating a list of prospective operations, the appliance reaction section 12 may create a list which already reflects the modification result. As a result, a learning of the process of generating prospective operations occurs by using biological signals from the user, thus gradually shifting to a state where no disappointment signal will be detected.

In the present embodiment, a method for supporting an ambiguous instruction from the user to "Turn on the TV" has been described. Furthermore, examples of ambiguous instructions such as "I want to watch baseball" and "Get me that" are illustrated in FIG. 6. However, various methods of modification are conceivable when a wrong inference is made in response to an ambiguous instruction given from the user.

An example may be a search through a large amount of photographs taken with a digital camera and stored in a personal computer, among which it would be difficult for the user to designate a specific content. When it is desired to search for a specific photograph, even if "a photograph from the amusement park" is designated, there may be a number of them, so that displaying a specific photograph may result in a wrong inference. In this case, too, if a disappointment occurs when a family photograph is presented, a family photograph which was taken in another place may be displayed for the case of the same category. For the case of a different category, a photograph of a scene without any people in it may be displayed, and so on.

Moreover, when the user wants to make a phone call, there may be a situation where a designation is to be made from within a list of phone numbers that is electronically stored in a personal computer, from which "Mr. A of a correspondent company", etc., may be designated. In this case, Mr. A may exist in a plurality of correspondent companies, or may be in the same correspondent company. In such a case, too, if it is the wrong person, a disappointment signal can be acquired from the electroencephalograms, and thus the user's desired search result can be quickly reached.

INDUSTRIAL APPLICABILITY

An information processing apparatus and information processing system according to the present invention includes a biological signal detection section and a signal analysis section. By analyzing a biological signal, it is possible to determine what in an operation of an appliance a disappointment is being felt about. Then, the content of processing is modified in accordance with the degree of disappointment. This will be useful for improving the interface of an information appliance or video/audio appliance or the like which performs exchanges of information with a user. Moreover, it can be implemented in and adapted to appliances, robots, and home appliance products which provide services to a user.

The invention claimed is:

1. An information processing system comprising:
   a reaction section for executing a first process based on a request from a user;
   an output section for outputting a result of a process;
   a signal detection section for measuring a signal concerning an event-related potential of electroencephalograms of the user;
   an analysis section for determining whether an elapsed time since the result is output and until a positive peak appears in the event-related potential is closer to a first reference time range or a second reference time range, the analysis section making the determination by defining the first reference time range to be 600±50 milliseconds and the second reference time range to be 750±50 milliseconds; and
   a reaction modifying section for determining a second process in accordance with the determination result,
   wherein the reaction section executes a second process.

2. The information processing system of claim 1, further comprising a storage section for retaining a plurality of parameters to be used for executing a process,
   wherein the plurality of parameters are each categorizable into a plurality of categories, and
   wherein the reaction modifying section is operable to:
   select a parameter belonging to a different category from that of the parameter used for the first process, when receiving a determination result indicating that the elapsed time is close to the first reference time range of 600±50 milliseconds;
   select a parameter belonging to the same category as that of the parameter used for the first process, when receiving a determination result indicating that the elapsed time is close to the second reference time range of 750±50 milliseconds; and
   determine a process using the selected parameter as the second process.

3. The information processing system of claim 2, wherein, the storage section retains history information indicating a frequency of use of each parameter; and
   the reaction section selects a parameter based on the history information, and executes the first process by using the selected parameter.

4. The information processing system of claim 3, wherein the reaction modifying section determines the second process by selecting, among the parameters which are yet to be selected, a parameter having a highest frequency of use.

5. The information processing system of claim 3, wherein, in response to execution of the second process, the storage section updates the history information of the parameter used for the second process.

6. The information processing system of claim 1, wherein, regarding a first content and a second content including at least one of video and audio,
   the reaction section executes an outputting process of the first content as the first process, and executes an outputting process of the second content which is different from the first content as the second process.

7. An information processing apparatus for being connected to an input device, an output device, and a signal detection device,
   the input device including means for receiving a request from a user,
   the output device including means for outputting a received signal,
   the signal detection device including means for measuring a signal concerning an event-related potential of electroencephalograms of the user, and
   the information processing apparatus comprising:
   a reaction section for executing a first process based on the request of the user from the input device and outputting a signal;
   an analysis section for, based on the signal concerning the event-related potential, identifying a positive peak in the event-related potential, and determining whether an elapsed time since the result is output and until the peak appears is closer to a first reference time range or a second reference time range, the analysis section making the determination by defining the first reference time range to be 600±50 milliseconds and the second reference time range to be 750±50 milliseconds; and
   a reaction modifying section for determining a second process in accordance with the determination result,
   wherein the reaction section outputs a signal by executing the second process.

8. An information processing method comprising the steps of:
   executing a first process based on a request from a user;
   outputting a result of a process;
   measuring a signal concerning an event-related potential of electroencephalograms of the user;
   identifying a positive peak in the event-related potential;
   determining whether an elapsed time since the result is output and until the peak appears is closer to a first reference time range or a second reference time range, the determination being made by defining the first reference time range to be 600±50 milliseconds and the second reference time range to be 750±50 milliseconds;
   determining a second process in accordance with the determination result; and
   executing a second process.

* * * * *